US011649219B2

(12) United States Patent
Bristow (10) Patent No.: US 11,649,219 B2
(45) Date of Patent: May 16, 2023

(54) PROCESS FOR PREPARING A CLOMAZONE, NOVEL FORM AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

(*) Notice: Subject to any disclaimer, the term of this patent is extended or adjusted under 35 U.S.C. 154(b) by 231 days.

(21) Appl. No.: 16/406,768

(22) Filed: May 8, 2019

(65) Prior Publication Data

US 2019/0284145 A1 Sep. 19, 2019

Related U.S. Application Data

(62) Division of application No. 14/902,118, filed as application No. PCT/CN2014/079805 on Jun. 13, 2014, now Pat. No. 10,316,004.

(30) Foreign Application Priority Data

Jul. 3, 2013 (GB) .................................. 1311938.3

(51) Int. Cl.
C07D 261/04 (2006.01)
A01N 43/80 (2006.01)
(52) U.S. Cl.
CPC ........... C07D 261/04 (2013.01); A01N 43/80 (2013.01); *C07B 2200/13* (2013.01)
(58) Field of Classification Search
None
See application file for complete search history.

(56) References Cited

U.S. PATENT DOCUMENTS

| 4,405,357 | A | ‡ | 9/1983 | Chang .................... A01N 37/28 504/27 |
| 4,552,585 | A | * | 11/1985 | Chang .................... A01N 43/72 504/223 |
| 4,742,176 | A | ‡ | 5/1988 | Guiducci ............. C07D 261/04 540/35 |
| 6,306,886 | B1 | * | 10/2001 | Maurin ................... A61P 35/00 514/378 |
| 6,555,572 | B2 | ‡ | 4/2003 | Lauener ................ C07C 255/46 514/445 |

FOREIGN PATENT DOCUMENTS

| CN | 1775765 | ‡ | 5/2006 |
| CN | 1775765 | A ‡ | 5/2006 |
| CN | 1775765 | A | 5/2006 |
| CN | 102050799 | A ‡ | 5/2011 |
| CN | 102060799 | ‡ | 5/2011 |
| CN | 102060799 | A | 5/2011 |
| CN | 102603664 | ‡ | 7/2012 |
| CN | 102603664 | A ‡ | 7/2012 |
| EA | 0016849 | B1 | 11/2009 |

OTHER PUBLICATIONS

Roberts, R.M. et al. Modern Experimental Organic Chemistry. Holt, Rinehart and Winston, New York, 1979, pp. 49-58.*
McClurg, R.B., "X-Ray Powder Diffraction (XRPD) to Describe Crystal Forms," Publication of SSCI an Aptuit Company, Jul. 9, 2008, pp. 1-23.*
International Search Report for Priority Application PCT/CN2014/079805 dated Sep. 1, 2014.‡
Tang D. X. et al. "Synthesis technique of clomazone and its approach to increase the quality", Modern Agrochemicals, vol. No. 5, Dec. 31, 2002 (Dec. 31, 2002). pp. 10-11.‡
International Search Report dated Sep. 1, 2014 (previously cited).‡
Kimberly, "Synthesis of 2-(2-chlorophenyl) Methyl-4, 4-dimethyl 3 isoxazolidinone", Research Degree Thesis [online], Available from http://www.research-degree-thesis.com/showinfo-67-637435-0.html [Accessed Jul. 21, 2013] (English Abstract translation included).‡
Yanbian Daxue Xuebao, Ziran Kexueban vol. 30(4), 2004, Li et al., pp. 270-273 and 306. See whole document especially the schemes also CAS abstract acc. No. 2006:194556. (English Abstract translation included).‡
French Search Report dated Mar. 24, 2015.‡
UK Search Report dated Jul. 30, 2013.‡
Yi, Lu, Research on Syntheses of the Herbicide Clomazone, Master Thesis, Nanjing University of Science and Technology, dated Jan. 18, 2004.‡
Liu, Weidong, Synthesis of Clomazone, Hunan Chemical Industry, 1999, 29(6): 32-33.‡

(Continued)

*Primary Examiner* — John Pak
(74) *Attorney, Agent, or Firm* — Dickinson Wright PLLC (57) ABSTRACT

A process for preparing clomazone is provided, the process comprising reacting 4,4-dimethyl-3-isoxazolidinone with 2-chlorobenzyl chloride in an aqueous medium in the presence of a base, in particular an alkali metal hydroxide. A method for preparing clomazone is also disclosed, the method comprising (a) crystallizing clomazone from solution in an organic solvent; and (b) isolating the resulting crystals. N-benzene is a particularly suitable solvent. Further, there is provided Form I crystalline 2-[(2-chlorophenyl) methyl]-4,4-dimethyl-3-isoxazolidinone (clomazone), wherein the polymorph Form I is characterized by at least one of the following properties:

(i) an X-ray powder diffraction pattern having characteristic peaks expressed in degrees $2\theta(+/-0.20°\ \theta)$ at one or more of the following positions: about 10.63, 16.07, 18.08, 19.11, 19.34, 21.20, 24.78 and 28.80; and (ii) an infrared (IR) spectrum having a characteristic peak: at about 2967 and 2870 $cm^{-1}$.

2 Claims, 2 Drawing Sheets

(56) References Cited

OTHER PUBLICATIONS

Research Degree Thesis directed to Synthesis of 2-(2-chlorophenyl) Methyl-4, 4-dimethyl-3-isoxazolidinone, available at http://www.research-degree-thesis.com/showinfo-67-637435-0.html at least on Jun. 3, 2014.‡

Roberts, R.M. et al. Modern Experimental Organic Chemistry. Third edition. Holt, Rinehart and Winston, New York. p. 582 (1979).‡

Rui, H.Z., "Synthesis of 1-(2-chlorophenyl)methyl-4,4-dimethyl-3-isoxazolidinone Master's Thesis," Jilin Univeristy, 2008 (original document in Chinese & partial English translation).‡

Barbara Rodrigues-Spong et al. "General principles of pharmaceutical solid polymorphism; a supramolecular perspective", Advanced Drug Delivery Reviews, 2004, 56, p. 241-274 (in particular, p. 242-243, 254)/D01:10.1016/j.addr.2003.10.005).

Mino R. Caira "Crystalline Polymorphism of Organic Compounds, Topics in Current Chemistry" 1998, vol. 198, p. 163-208 (in particular, p. 165-177)/DOI: https://doi.org/10.1007/3.540-69178-2.5).

Sherry L. Morisette et al. "High-throughout crystallization: polymorphs, salts, co-crystals and solvate of pharmaceutical solids", Advanced Drug Delivery Reviews, 2004, 56, p. 275-300 (ABSTRACT p. 287-297)/d01:10.1016/).addr.2003.10.020.

\* cited by examiner
‡ imported from a related application

PROCESS FOR PREPARING A CLOMAZONE, NOVEL FORM AND USE OF THE SAME

This U.S. divisional patent application claims the benefit of U.S. application Ser. No. 14/902,118 filed 30 Dec. 2015, which is a 371 national phase entry of PCT/CN2014/079805, filed 13 Jun. 2014 which claims benefit of GB Patent Application No. 1311938.3, filed 3 Jul. 2013, the entire contents of which are incorporated herein by reference for all purposes.

BACKGROUND

1. Field

The present disclosure relates to 2-[(2-chlorophenyl)methyl]-4,4-dimethyl-3-isoxazolidinone (Clomazone), an agricultural herbicide. The present disclosure relates in particular to novel crystalline polymorphs of clomazone, to processes for their preparation, and compositions comprising the same.

2. Description of Related Art

2-[(2-chlorophenyl)methyl]-4,4-dimethyl-3-isoxazolidinone, a compound having the common name clomazone, is disclosed in U.S. Pat. No. 4,405,357. Its herbicidal properties are described. This herbicidal isoxazolidinone is represented by the following structural formula (I):

I

U.S. Pat. No. 4,405,357 discloses the preparation of clomazone. In particular, the following procedure to synthesize clomazone is disclosed:

A further process scheme is disclosed in U.S. Pat. No. 4,405,357, as follows:

However, the process yields the desired product in only a relatively low yield due to the formation of by-products having the general formulae (II) and (III) as follows:

It is disclosed in U.S. Pat. No. 4,742,176 that the typical product mixture of the above process scheme includes the compounds of formulae (I), (II) and (III) in the ratio of (1):(II):(III) of about 85/10/5. It would be advantageous if an improved process could be found that yielded higher amounts of clomazone, with reduced formation of the by-products of formulae (II) and (III).

In addition, the process of U.S. Pat. No. 4,405,357 suffers an number of drawbacks. As indicated above, the reaction process utilizes methanol (MeOH) and dimethylformamide (DMF) as solvents. However, the use of the aforementioned solvents gives rise to a number of problems, in particular on a commercial scale of production. For example, methanol is a flammable, unsafe solvent with a low flash point and is a source for peroxide formation. As a result, the use of methanol in large-scale production is very limited. In addition, aprotic polar solvents, such as dimethyl formamide (DMF) are water-miscible and are typically recycled as azeotropes containing high amounts of water.

U.S. Pat. No. 4,742,176 discloses an improvement to the second process scheme of U.S. Pat. No. 4,405,357. In particular, the process is modified by contacting the product mixture with hydrogen chloride gas prior to isolating the desired product. This treatment converts the compound of formula (II) into a mixture of 4,4-dimethyl-3-isoxazolidinone and 2-chlorobenzyl chloride, which may be recycled with base to the desired product. The compound of formula (III) in the product is converted by contact with hydrogen chloride into other components, which are readily separated. Clomazone is not affected by contact with hydrogen chloride. As will be appreciated, these modifications result in a greater processing complexity and involve the use of additional components, in particular hydrogen chloride gas, which is undesirable.

To date, there are no simple methods for the synthesis of clomazone, which can be used on a large scale to produce the desired product to a high degree of purity.

There is thus an urgent and unmet need in the art for efficient methods for the preparation and purification of clomazone, which overcome the drawbacks and deficiencies of the prior art methods.

In addition, there are also no known crystalline polymorphic forms of clomazone.

SUMMARY

An improved process for the preparing of clomazone has been found, the process avoiding the need for the solvents used in the prior art processes, as disclosed above, reduces the formation of side products, thereby reducing the need for extensive purification steps, and provides clomazone in high yields. The process is particularly suitable for use for the manufacture of clomazone on a commercial scale.

In a first aspect, the invention provides a process for preparing clomazone, the process comprising:

reacting 4,4-dimethyl-3-isoxazolidinone with 2-chlorobenzyl chloride in an aqueous medium in the presence of a base.

It has surprisingly been found that clomazone may be formed in high yields by the reaction of 4,4-dimethyl-3-isoxazolidinone with 2-chlorobenzyl chloride in the presence of a base using water a solvent. The ability to use water is a significant advantage over the known processes and avoids the need to use solvents such as methanol and dimethylformamide, discussed above. The process produces clomazone in high purity, avoiding the need to subject the product mixture to extensive separation techniques. Rather, it has been found that clomazone may be recovered from the reaction mixture by simple crystallization techniques.

In a second aspect, is provided a novel polymorph crystalline form of clomazone, herein designated as 'Form I', and described in more detail below.

BRIEF DESCRIPTION OF DRAWINGS

The aspects and embodiments of the invention can be more clearly understood by reference to the following drawings, which are intended to illustrate, but not limit, the claimed invention.

DETAILED DESCRIPTION OF SPECIFIC EMBODIMENTS

The reaction of 4,4-dimethyl-3-isoxazolidinone with 2-chlorobenzyl chloride is conducted in an aqueous medium in the presence of a base. Suitable bases include one or a mixture of hydroxides, carbonates, and hydrides. Suitable bases include metal and ammonium compounds, with metal compounds being preferred, in particular alkali and alkaline earth metal bases. Alkali metal bases are particularly preferred. The base is preferably a carbonate or hydroxide, with alkali metal carbonates and hydroxides being preferred bases. Preferred alkali metals are sodium and potassium. Sodium hydroxide is one particularly preferred base. Potassium hydroxide is also a preferred base. Sodium carbonate and potassium carbonate are further particularly preferred bases.

The reaction of 4,4-dimethyl-3-isoxazolidinone with 2-chlorobenzyl chloride is conducted under basic conditions. Preferably, the pH of the reaction mixture is from 7.5 to 9.5, more preferably from 8.5 to 9.5.

The reaction sequence may be represented as follows:

4,4-dimethyl-3-isoxazolidinone    2-chlorobenzyl chloride 2-(2-chlorobenzyl)-4,4-dimethyl-1,2-
oxazolidin-3-one

3-chloro-N-hydroxy-2,2-
dimethylpropanamide

The reaction mixture is preferably heated. Suitable temperatures are in the range of from 50 to 95° C., more preferably from 60 to 90° C. A reaction temperature of about 85° C. has been found to be very suitable.

4,4-dimethyl-3-isoxazolidinone may be prepared by cyclizing 3-chloro-N-hydroxy-2,2-dimethylpropanamide with a base. Suitable bases are those bases noted above. Again, a preferred base is an alkali metal hydroxide, in particular sodium hydroxide. It is particularly preferred to conduct the cyclizing of 3-chloro-N-hydroxy-2,2-dimethylpropanamide with the base in a solvent, in particular in an aqueous medium using water as a solvent.

The cyclizing of 3-chloro-N-hydroxy-2,2-dimethylpropanamide is conducted under basic conditions. Preferably, the pH of the reaction mixture is from 7.5 to 9.5.

This reaction sequence may be represented as follows:

3-chloro-N-hydroxy-2,2-
dimethylpropanamide

4,4-dimethyl-3-
isoxazolidinone

The reaction mixture is preferably heated. Suitable temperatures are in the range of from 20 to 60° C., more preferably from 30 to 50° C. A reaction temperature of about 45° C. has been found to be very suitable.

3-chloro-N-hydroxy-2,2-dimethylpropanamide may be prepared by the reaction of 3-chloro-2,2-dimethylpropanoyl chloride with hydroxylamine hydrochloride (NH₂OH.HCl) in the presence of a base. Suitable bases are those bases noted above. Again, a preferred base is an alkali metal hydroxide, in particular sodium hydroxide. It is particularly preferred to conduct the reaction of 3-chloro-2,2-dimethylpropanoyl chloride with hydroxylamine hydrochloride base in the presence of a solvent, in particular an aqueous medium using water as a solvent.

The reaction of 3-chloro-2,2-dimethylpropanoyl chloride with hydroxylamine hydrochloride is conducted under basic conditions. Preferably, the pH of the reaction mixture is from 7.0 to 9.5, more preferably from 7.0 to 8.5, still more preferably from 7.0 to 7.5.

This reaction sequence may be represented as follows:

3-Chloro-2,2-
dimethylpropanoyl chloride

The reaction mixture is preferably heated. Suitable temperatures are in the range of from 50 to 95° C., more preferably from 60 to 90° C. A reaction temperature of about 85° C. has been found to be very suitable.

It is a particular advantage of the reaction scheme described above for the preparation of clomazone from 3-chloro-2,2-dimethylpropanoyl chloride that all steps in the reaction sequence may be carried out in an aqueous medium using water as a solvent, in particular for the base employed. It is a further advantage that the same base may be used throughout the aforementioned series of reactions.

As noted above, the process described hereinbefore yields clomazone in high yields with little formation of by-products. As a result, clomazone may be extracted from the reaction mixture by simple crystallization, without the need for extensive separation and purification techniques.

In a further aspect, the present invention provides a method for preparing clomazone, the method comprising:

(a) crystallizing clomazone from solution in an organic solvent; and (b) isolating the resulting crystals.

Clomazone is barely soluble in water. However, clomazone may be dissolved into a range of organic solvents. The method of the present invention isolates crystals of clomazone after crystallization from a solution in an organic solvent. The method may employ a single solvent or a mixture of organic solvents. Preferred solvents are organic solvents selected from formamides, such as dimethylformamide, benzene and substituted benzene derivatives, such as toluene, nitriles, such as acetonitrile, halogenated alkanes, such as methylene chloride, alkanes, such as hexanes, in particular n-hexane, and mixtures thereof. The solvent is preferably non-polar. Particularly preferred non-polar solvents are alkanes, more preferably aliphatic alkanes, in particular normal or straight chain alkanes. A particularly preferred solvent for use in the method of this aspect of the present invention is an alkane having from 6 to 10 carbon atoms, more preferably from 6 to 8 carbon atoms, especially hexane, with n-hexane especially preferred.

In the method of the present invention, clomazone is dissolved in the organic solvent, preferably with heating. The resulting solution is cooled and crystals of clomazone allowed to form. The crystalline product is then isolated from the organic solvent. Techniques and equipment for preparing the solution of clomazone in the organic solvent, crystallizing clomazone and isolating the crystalline product are known in the art and are commercially available.

In the process of the first aspect of the present invention, clomazone may be separated from the final reaction medium by dissolving the clomazone in the organic solvent and subjecting the resulting solution to the method of the second aspect of the present invention.

Surprisingly, it has been found that clomazone prepared by the above method of crystallization is obtained in a novel polymorph crystalline form, herein designated as 'Form I'.

Accordingly, in a further aspect, the present invention provides Form I crystalline 2-[(2-chlorophenyl)methyl]-4,4- dimethyl-3-isoxazolidinone (clomazone), wherein the polymorph Form I is characterized by at least one of the following properties:

(i) an X-ray powder diffraction pattern having characteristic peaks expressed in degrees 2θ(+/−0.20° θ) at one or more of the following positions: about 10.63, 16.07, 18.08, 19.11, 19.34, 21.20, 24.78 and 28.80; and (ii) an infrared (IR) spectrum having a characteristic peak: at about 2967 and 2870 cm$^{-1}$.

Figure 1:
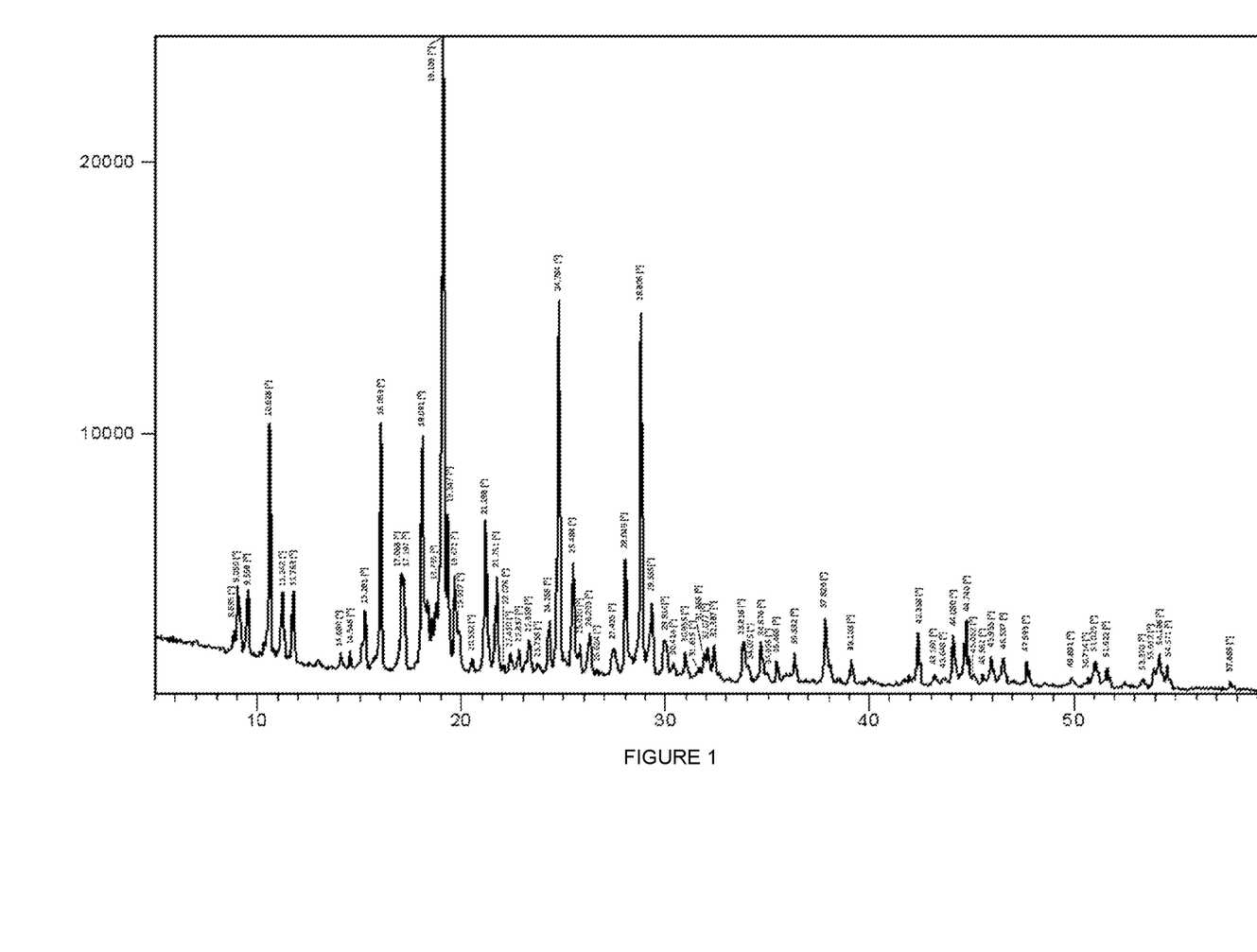
FIG. 1 is graph showing an X-ray diffractogram of the polymorph crystalline form of clomazone (Form I) showing an infrared (IR) spectrum of the polymorph crystalline form of clomazone (Form I).

The X-ray powder diffraction pattern of the Form I crystalline polymorph of clomazone is shown in FIG. 1. As can be seen, Form I exhibits an X-ray powder diffraction pattern having characteristic peaks (expressed in degrees 2θ (+/−0.2° θ) at one or more of the following positions: 10.63, 16.07, 18.08, 19.11, 19.34, 21.20, 24.78 and 28.80.

Figure 2:
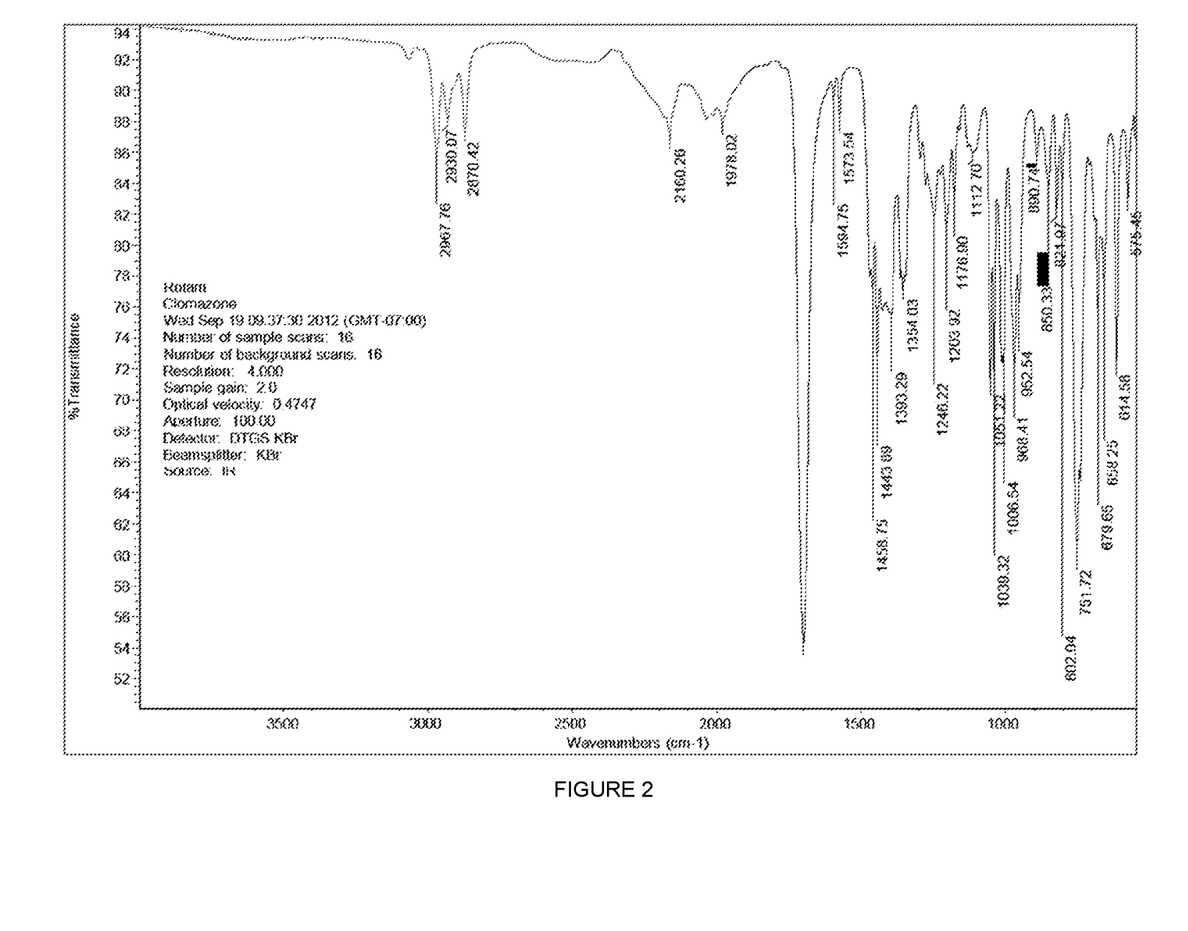
FIG. 2 is a graph showing an infrared (IR) spectrum of the polymorph crystalline form of clomazone (Form I).

The infrared (IR) spectrum of Form I is shown in FIG. 2. As can be seen, Form I exhibits an infrared (IR) spectrum at the 3000 cm$^{-1}$ range having a characteristic peak at about 2967 and 2870 cm$^{-1}$.

As noted above, Form I of clomazone is obtainable by the method described above. In particular, this form of clomazone may be obtained by crystallization of clomazone from solution in an organic solvent, most particularly hexane, acetonitrile, methylene chloride, dimethylformamide, toluene, and mixtures thereof.

Clomazone prepared by the process and method of the present invention and Form I clomazone may be used as a herbicide in the control of unwanted plant growth. Formulations and techniques for the use of clomazone in the control of plant growth are known in the art.

In further aspect, the present invention provides a method of controlling plant growth at a locus, the method comprising applying to the locus a formulation comprising clomazone prepared by a process or method as hereinbefore described or comprising Form I clomazone.

In a still further aspect, the present invention provides the use of clomazone prepared by a process or method as hereinbefore described or Form I clomazone in the control of plant growth.

The crystalline Form I of clomazone can be used as such, in the form of a formulation thereof or the use forms prepared therefrom. For example, clomazone Form I may be used in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes. In particular, they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The following are examples of formulations of the clomazone products of the present invention: 1. Products for dilution with water for foliar applications. The formulations may also be applied to seeds, either with or without dilution, for seed treatment purposes.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 80 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF) (for Seed Treatment Purposes Only)

In an agitated ball mill, 20 parts by weight of the active compound(s) are comminuted with addition of 10 parts by weight of dispersants, 1 part by weight of a gelling agent/wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted.

I) Dustable Powders (DP, DS)

5 parts by weight of the active compound(s) are ground finely and mixed intimately with 95 parts by weight of finely divided kaolin. This formulation gives a dustable product having 5% (w/w) of active compound(s).

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods for preparing granules include extrusion, spray-drying or use of a fluidized bed. This gives granules to be applied undiluted for foliar use.

K) Microcapsulation, ME 0.5 parts by weight of the active compound(s) is ground finely and associated with 95.5 parts by weight of a mixture of polyurea, crosslinker, and carriers, whereby a formulation with 0.5% (w/w) of active compound(s) is obtained. This gives a microencapsulation product having 5% (w/w) of active compound(s), in which the active clomazone ingredient is encapsulated within microcapsules having a polymer shell.

L) Microcapsulation Granules, MEG 0.5 part by weight of the active compound(s) is ground finely and associated with 95.5 parts by weight of polyurea, crosslinker, a solid carrier and a binder to form a mixture, forming granules from the resulting mixture; applying a composition comprising a binder to coat the granules; and drying the thus coated granules. This procedure gives a microencapsulated active ingredient within Granules having 5% (w/w) of active compound(s).

Embodiments of the present invention are illustrated by the following specific Examples.

EXAMPLES

Example 1: Synthesis of Clomazone

Step 1: Preparation of 3-chloro-N-hydroxy-2, 2-dimethylpropanamide (CNHP)

3-chloro-N-hydroxy-2, 2-dimethylpropanamide was prepared by way of the following general reaction path:

3-Chloro-2,2-dimethylpropanoyl chloride 3-chloro-N-hydroxy-2,2-dimethylpropanamide 1200 kg of water was charged into a 4000 L reactor, followed by 318 kg of hydroxylamine hydrochloride (NH$_2$OH·HCl). The resulting mixture was stirred at room temperature until the hydroxylamine hydrochloride was dissolved completely in the water. 50% Sodium hydroxide aqueous solution was added dropwise into the reactor over a period of 1.5 h to adjust the pH to a value of from 7.0 to 7.5, with the temperature maintained at 20 to 25° C. After the addition of sodium hydroxide solution was completed, 713 kg of 3-chloro-2, 2-dimethylpropanoyl chloride was added dropwise into the reaction mixture over a period of 3 h. The reaction mixture was stirred while maintaining the aforementioned temperature until the reaction was complete.

The resulting mixture was cooled to 5 to 10° C. and held at this temperature with stirring for a period of 1.5 h. The resulting mixture was filtered to isolate the solid material. The resulting solid material was dried under high vacuum. The resulting crude product was further purified in acetone to give pure 3-chloro-N-hydroxy-2, 2-dimethylpropanamide (645 kg, purity: 98%, Yield: 92%).

Step 2: Preparation of 4, 4-dimethyl-3-isoxazolidinone (010)

4, 4-dimethyl-3-isoxazolidinone was prepared from the product of Step 1 by way of the following general reaction path:

3-chloro-N-hydroxy-2,2-dimethylpropanamide        4,4-dimethyl-3-isoxazolidinone

1000 kg of water was charged into a 3000 L reactor then 640 kg of 3-chloro-N-hydroxy-2, 2-dimethylpropanamide was added. The resulting solution was stirred at room temperature for 1 h, and thereafter the temperature was raised to 45° C. 50% Sodium hydroxide aqueous solution was added dropwise to the resulting mixture over a period of 5 hours. After the addition of sodium hydroxide was completed, the resulting mixture was stirred at room temperature until the reaction had completed.

The resulting solution was cooled to 5 to 10° C. and held at this temperature with stirring for a further 3 h. The resulting mixture was filtered to isolate a solid product. The solid was washed with water and dried under high vacuum to give pure 4, 4-dimethyl-3-isoxazolidinone (about 466 kg, purity: 96%: yield: 93%).

Step 3: Preparation of 2-(2-chlorobenzyl)-4,4-dimethyl-1,2-oxazolidin-3-one (Clomazone)

Clomazone was prepared from the product of Step 2 by way of the following general reaction path:

4,4-dimethyl-3-isoxazolidinone        2-chlorobenzyl chloride 2-(2-chlorobenzyl)-4,4-dimethyl-1,2-oxazolidin-3-one 1000 kg of water was charged to a 4000 L reactor, then 460 kg of 4, 4-dimethyl-3-isoxazolidinone was added. The resulting solution was stirred at room temperature for 1 h. Thereafter, 383 kg of $Na_2CO_3$ was added in small portions. The temperature of the resulting mixture was raised to 85° C. and the mixture stirred at this temperature for 2 h. Thereafter, 672 kg of 2-chlorobenzyl chloride was added dropwise over a period of 5 h at 85° C. After the addition was completed, the resulting solution was stirred at the same temperature until the reaction had completed.

The resulting mixture was cooled to room temperature and 800 kg of dichloromethane was added to the reactor. The resulting mixture was stirred at room temperature for 15 h. Thereafter, the aqueous phase was separated, extracted with dichloromethane (3 times). Dichloromethane was recovered by distillation and then 2000 kg of hexane was added into the reactor. The resulting mixture was refluxed for 1 h, then cooled to 10 to 15° C. and stirred for another 1 h.

The solid material was isolated by filtration. The solid was washed with hexanes several times and dried under high vacuum to give pure clomazone Technical (815 kg, Purity: 96%).

Similar results are obtained using sodium hydroxide as the base, in place of sodium carbonate.

Example 2: Preparation of Clomazone Form I 2 g of clomazone was heated in 10 g of hexane until complete dissolution. The resulting solution was refluxed for 1 h, then cooled to 10 to 15° C. and stirred for another 1 h. The resulting mixture was filtered to isolate a solid. The resulting solid was washed with hexanes several times and dried under high vacuum to give crystals of pure clomazone technical (815 kg, Purity: 96%).

The crystals were characterized as being of clomazone Form I using both infrared (IR) spectrometry and x-ray diffraction.

The IR spectrum of the Form I clomazone is set out in FIG. 2. The IR spectrum exhibits characteristic peaks at 2967 and 2870 cm-1.

Form I clomazone has the X-ray powder diffractogram shown in FIG. 1 with the reflexes listed in Table 1 below.

TABLE 1

| 2 θ and d-value of modification I ||
|---|---|
| 2 θ (°) | d (Å) |
| 10.63, ± 0.2 | 8.32 ± 0.05 |
| 16.07, ± 0.2 | 5.52 ± 0.03 |
| 18.08, ± 0.2 | 4.90 ± 0.03 |
| 19.11,. ± 0.2 | 4.64 ± 0.02 |
| 19.34, ± 0.2 | 4.59 ± 0.02 |
| 21.20, ± 0.2 | 4.19 ± 0.02 |
| 24.78 ± 0.2 | 3.59 ± 0.02 |
| 28.80 ± 0.2 | 3.10 ± 0.02 |

The x-ray diffractogram was determined using the following parameters:
Wavelength
Intended wavelength type: Kα
Kα1 (Å): 1.540598
Kα2 (Å): 1.544426
Kα2/Kα1 intensity ratio: 0.50
Kα (Å): 1.541874
Kβ (Å): 1.392250
Incident Beam Path
Radius (mm): 240.0
X-Ray Tube
Name: PW3373/10 Cu LFF DK185240
Anode material: Cu
Voltage (kV): 40
Current (mA): 40
Focus
Focus type: Line
Length (mm): 12.0
width (mm): 0.4
Take-off angle (°): 6.0
Soller Slit
Name: Soller 0.04 rad.
Opening (rad.): 0.04
Mask
Name: Inc. Mask Fixed 15 mm (MPD/MRD)
Width (mm): 11.60
Anti-Scatter Slit
Name: Slit Fixed ½°
Type: Fixed
Height (mm): 0.76
Divergence Slit
Name: Slit Fixed 1°
Distance to sample (mm): 140
Type: Fixed
Height (mm): 0.38
Diffracted Beam Path
Radius (mm): 240.0
Anti-Scatter Slit
Name: AS Slit 5.5 mm (X'Celerator)
Type: Fixed
Height (mm): 5.50
Filter
Name: Nickel
Thickness (mm): 0.020
Material: Ni
Detector
Name: X'Celerator
Type: RTMS detector
Mode: Scanning
Active length (°): 2.122
Source
Created by: Soochow University
Application SW: X'Pert Data Collector vs. 2.1a
Instrument control SW: XPERT-PRO vs. 1.6
Instrument ID: 0000000026005495
Scan axis: Gonio
Scan range (°): 3.0150-60.0004
Step size (°): 0.0334
No. of points: 1705
Scan mode: Continuous Example 3: Preparation of Form I Clomazone 2 g of clomazone prepared as described in Example 1 and 10 g of acetonitrile were heated until complete dissolution. The resulting mixture was refluxed for 1 h, then cooled to 10 to 15° C. and stirred for a further 1 h. The resulting mixture was filtered to isolate a solid. After filtration, the solid was washed with acetonitrile several times and dried under high vacuum to give crystals of pure clomazone technical (815 kg, Purity: 96%). The crystals were characterized as being clomazone Form I using infra red spectrometry and x-ray diffraction as described in Example 2.

Example 4: Preparation of Form I Clomazone 2 g of clomazone prepared as described in Example 1 was dissolved in 10 g of methylene chloride while applying low heating over a heating plate. The resulting mixture was refluxed for 1 h, then cooled to 10 to 15° C. and stirred for another 1 h. The resulting mixture was filtered to isolate a solid. After filtration, the solid was washed with methylene chloride several times and dried under high vacuum to give crystals of pure clomazone technical (815 kg, Purity: 96%). The crystals were characterized as being clomazone Form I using infra red spectrometry and x-ray diffraction as described in Example 2.

Example 5: Preparation of Form I Clomazone 2 g of clomazone prepared as described in Example 1 and 10 g of dimethyl formamide (DMF) were heated until complete dissolution of the clomazone was reached. The resulting mixture was refluxed for 1 h, then cooled to 10 to 15° C. and stirred for another 1 h. The resulting mixture was filtered to isolate a solid. After filtration, the solid was washed with DMF several times and dried under high vacuum to give crystals of pure clomazone technical (815 kg, Purity: 96%). The crystals were characterized as being clomazone Form I using infra red spectrometry and x-ray diffraction as described in Example 2.

Example 6: Preparation of Form I Clomazone 2 g of clomazone as prepared in Example 1 and 10 g of toluene were heated until complete dissolution of the clomazone was reached. The resulting mixture was refluxed for 1 h, then cooled to 10 to 15° C. and stirred for a further 1 h. The resulting mixture was filtered to isolate a solid. After filtration, the solid was washed with toluene several times and dried under high vacuum to give crystals of pure clomazone technical (815 kg, Purity: 96%). The crystals were characterized as being clomazone Form I using infra red spectrometry and x-ray diffraction as described in Example 2.

Example 7: Preparation of Form I Clomazone 2 g of clomazone prepared as described in Example 1 and 10 g of an equal parts mixture of DMF and toluene were heated until complete dissolution of the solid clomazone was reached. The resulting mixture was refluxed for 1 h, then cooled to 10 to 15° C. and stirred for a further 1 h. The resulting mixture was filtered to isolate a solid. After filtration, the solid was washed with an equal parts mixture of DMF and toluene several times and dried under high vacuum to give crystals of pure clomazone technical (815 kg, Purity: 96%). The crystals were characterized as being clomazone Form I using infra red spectrometry and x-ray diffraction as described in Example 2.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A crystalline polymorph (Form I) of 2-[(2-chlorophenyl)methyl]-4,4-dimethyl-3-isoxazolidinone (clomazone), wherein the polymorph Form I has the following properties: (i) an X-ray powder diffraction pattern having characteristic peaks expressed in degrees 2θ(+/−0.20° θ) at the following positions: about 10.63, 16.07, 18.08, 19.11, 19.34, 21.20, 24.78 and 28.80; and (ii) an infrared (IR) spectrum having a characteristic peak: at about 2967 and 2870 cm$^{-1}$.

2. A method of controlling plant growth at a locus, the method comprising applying to the locus a formulation comprising clomazone in crystalline polymorph Form I, according to claim 1.

* * * * *